United States Patent [19]

Benjamin et al.

[11] Patent Number: 4,782,047

[45] Date of Patent: Nov. 1, 1988

[54] AQUEOUS STEROID FORMULATIONS FOR NASAL ADMINISTRATION

[75] Inventors: Eric Benjamin, Sunnyvale; Shabbir Anik, Mountain View; Ya-Yun T. Lin, Cupertino, all of Calif.

[73] Assignee: Syntex Pharmaceuticals International Ltd., Hamilton, Bermuda

[21] Appl. No.: 866,171

[22] Filed: May 22, 1986

[51] Int. Cl.⁴ .................. A61K 31/58; A61K 31/56
[52] U.S. Cl. .................................. 514/174; 514/169
[58] Field of Search ................... 514/174, 180, 169

[56] References Cited

U.S. PATENT DOCUMENTS 4,444,762  4/1984  Rajadhyaksha .................. 424/88

OTHER PUBLICATIONS

Physician's Desk Reference, 38th ed. (1984), p. 1981; Nasalide ®.

Primary Examiner—Leonard Schenkman
Assistant Examiner—Joseph A. Lipovsky
Attorney, Agent, or Firm—David A. Lowin; Tom M. Moran; Grant D. Green

[57] ABSTRACT

A non-stinging aqueous anti-inflammatory steroid formulation suitable for intranasal administration comprises: an anti-inflammatory steroid in an amount between about 0.01% and about 0.05% (w/v); propylene glycol in an amount between about 2% and about 10% (w/v); PEG 400 in an amount between about 10% and about 25% (w/v); polysorbate 20 in an amount between about 1% and about 4% (w/v); an effective amount of a preservative; an effective amount of a stabilizer; an effective amount of an antioxidant; water; and pH buffering agent sufficient to adjust the pH of the resulting solution to between about 3.5 and about 7.

15 Claims, No Drawings

AQUEOUS STEROID FORMULATIONS FOR NASAL ADMINISTRATION

BACKGROUND OF THE INVENTION

1. Field of the Invention

This invention relates to aqueous anti-inflammatory steroid formulations suitable for nasal administration, and to methods for treating inflammation of the nasal mucosa by intranasal administration of said formulations.

2. Related Disclosure

Acceptable formulations must be able to dissolve or suspend an active compound without precipitation or undue oxidation of the components. In other words, acceptable formulations must be stable. Acceptable formulations must also avoid creating discomfort upon administration, and will employ only pharmaceutically acceptable components. Finally, acceptable formulations must not support the growth of microorganisms, and so generally include preservatives.

Anti-inflammatory steroids are difficult to formulate in aqueous solutions due to their generally low solubility in water. Aqueous formulations of anti-inflammatory steroids such as flunisolide suitable for nasal administration are commercially available, for example under the trademark Nasalide®. However, currently available formulations, while safe and effective, are known to cause stinging upon administration in some cases, which is a side effect particularly undesirable when treating nasal inflammation. The novel formulations of the invention are stable, effectively preservable, and are suitable for nasal administration of anti-inflammatory steroids without causing stinging.

SUMMARY OF THE INVENTION

One aspect of the invention is a stable, preservable, substantially non-stinging aqueous anti-inflammatory steroid formulation suitable for nasal administration, which formulation comprises: an anti-inflammatory steroid in an amount between about 0.01% and about 0.05% (w/v); propylene glycol in an amount between about 2% and about 10% (w/v); PEG 400 in an amount between about 10% and about 25% (w/v); polysorbate 20 in an amount between about 1% and about 4% (w/v); an effective amount of a preservative, preferably between about 0.02% and about 0.08% (w/v); an effective amount of an antioxidant, preferably between about 0.001% and 0.05% (w/v); an effective amount of a stabilizer, preferably between about 0.005% and 0.05%; water; and pH buffering agent sufficient to adjust the pH of the resulting solution to between about 3.5 and about 7.

Another aspect of the invention is a method of treating inflammation of the nasal mucosa without inducing stinging, which method comprises intranasally administering to a subject in need thereof a substantially non-stinging aqueous anti-inflammatory steroid formulation as described above.

DETAILED DESCRIPTION AND PREFERRED EMBODIMENTS

One aspect of the invention is a stable, preservable, substantially non-stinging aqueous anti-inflammatory steroid formulation suitable for nasal administration, which formulation comprises: an anti-inflammatory steroid in an amount between about 0.01% and about 0.05% (w/v); propylene glycol in an amount between about 2% and about 10% (w/v); PEG 400 in an amount between about 10% and about 25% (w/v); polysorbate 20 in an amount between about 1% and about 4% (w/v); an effective amount of a preservative, preferably between about 0.02% and about 0.08% (w/v); an effective amount of a stabilizer, preferably between about 0.005% and about 0.05%; an effective amount of an antioxidant, preferably between about 0.001% and about 0.05%; water; and a pH buffering agent sufficient to adjust the pH of the resulting solution to between about 3.5 and about 7. A preferred subgenus of the invention is the formulation wherein said anti-inflammatory steroid is flunisolide, particularly in an amount of about 0.025% (w/v). A preferred class is the formulation wherein said preservative is benzalkonium chloride in an amount between about 0.02% and about 0.08% (w/v); said stabilizer is disodium EDTA in an amount between about 0.005% and about 0.05% (w/v); and said antioxidant is BHT in an amount between about 0.001% and about 0.05% (w/v); especially the formulation which further comprises sorbitol in an amount between about 0.001% and about 5% (w/v). A preferred subclass is the formulation wherein said pH buffering agent comprises: citric acid in an amount between about 0.001% and about 0.05% (w/v); and sodium citrate dihydrate in an amount between about 0.001% and about 0.05% (w/v). A preferred species is the non-stinging aqueous anti-inflammatory steroid formulation suitable for nasal administration, which formulation comprises:

flunisolide hemihydrate in an amount of about 0.025% (w/v);
propylene glycol in an amount of about 5% (w/v);
PEG 400 in an amount of about 20% (w/v);
polysorbate 20 in an amount of about 2.50% (w/v);
benzalkonium chloride in an amount of about 0.035% (w/v);
disodium EDTA in an amount of about 0.01% (w/v);
BHT in an amount of about 0.01% (w/v);
citric acid in an amount of about 0.005% (w/v);
sodium citrate dihydrate in an amount of about 0.00765% (w/v);
sorbitol in an amount of about 2.00% (w/v); and
water, wherein the pH of the resulting solution is adjusted to about 5.2.

Another aspect of the invention is a method of treating inflammation of the nasal mucosa without inducing stinging, which method comprises intranasally administering to a subject in need thereof a substantially non-stinging aqueous anti-inflammatory steroid formulation comprising an anti-inflammatory steroid in an amount between about 0.01% and about 0.05% (w/v); propylene glycol in an amount between about 2% and about 10% (w/v); PEG 400 in an amount between about 10% and about 25% (w/v); polysorbate 20 in an amount between about 1% and about 4% (w/v); an effective amount of a preservative, preferably between about 0.02% and about 0.08% (w/v); an effective amount of a stabilizer, preferably between about 0.005% and about 0.05%; an effective amount of an antioxidant, preferably between about 0.001% and about 0.05%; water; and a pH buffering agent sufficient to adjust the pH of the resulting solution to between about 3.5 and about 7; and water. A preferred subgenus is the method wherein said anti-inflammatory steroid is flunisolide in an amount of about 0.025% (w/v), particularly where said preservative is benzalkonium chloride in an amount between about 0.02% and about 0.08% (w/v); said stabilizer is disodium EDTA in an amount between about 0.005% and about 0.05% (w/v); and said antioxidant is BHT in an amount between about 0.001% and about 0.05% (w/v). A preferred class is the method which further comprises sorbitol in an amount between about 0.001% and about 5% (w/v). A preferred subclass is the method wherein said pH buffering agent comprises citric acid in an amount between about 0.001% and about 0.05% (w/v); and sodium citrate dihydrate in an amount between about 0.001% and about 0.05% (w/v). A preferred species of the invention is the method of treating inflammation of the nasal mucosa without inducing stinging, which method comprises intranasally administering to a subject in need thereof a substantially non-stinging aqueous anti-inflammatory steroid formulation comprising flunisolide hemihydrate in an amount of about 0.025% (w/v);
propylene glycol in an amount of about 5% (w/v);
PEG 400 in an amount of about 20% (w/v);
polysorbate 20 in an amount of about 2.50% (w/v);
benzalkonium chloride in an amount of about 0.035% (w/v);
disodium EDTA in an amount of about 0.01% (w/v);
BHT in an amount of about 0.01% (w/v);
citric acid in an amount of about 0.005% (w/v);
sodium citrate dihydrate in an amount of about 0.00765% (w/v);
sorbitol in an amount of about 2.00% (w/v); and
water, wherein the pH of the resulting solution is adjusted to about 5.2.

DEFINITIONS

As used herein, the term "anti-inflammatory steroid" refers to a steroid compound which is pharmaceutically acceptable, and which is known to be useful in reducing inflammation. Particularly suitable anti-inflammatory steroids are flunisolide and beclomethasone. Flunisolide is most advantageously used in the form of the hemihydrate, as that form is non-hygroscopic and is thus easiest to handle curing formulation. Flunisolide is commercially available, and can be prepared as described in U.S. Pat. No. 4,273,710, incorporated herein by reference. Beclomethasone is also commercially available, and can be prepared as described in G.B. Pat. No. 912,378.

Propylene glycol refers to 1,2-propanediol. Propylene glycol is available commercially.

Polyethylene glycol 400 refers to commercially available mixtures of polymers of the form H—(OCH$_2$CH$_2$)$_n$—OH, where the average value of n is between 8.2 and 9.1. Polyethylene glycol 400 is abbreviated herein as "PEG 400."

Polysorbate 20 refers to commercially available polyoxyethylene-sorbitan monoesters, for example Tween® 20.

The term "BHT" refers to butylated hydroxytoluene, which is a commercially available preservative/antioxidant.

The term "BHA" refers to butylated hydroxyanisole, which is a commercially available preservative/antioxidant.

The term "preservative" refers to a compound or mixture of compounds used in a formulation which is useful for reducing or eliminating microbial growth in a formulation. A preservative must be pharmaceutically acceptable at the concentrations used, and should not interfere with the action of the active compound in the formulation. An "effective amount" of a preservative is that amount necessary to prevent the growth of microorganisms in the formulation. The effective amount may be determined using the USP-BP modified double blind assay. Exemplary preservatives include, without limitation, BHA, BHT, thimerosal, potassium sorbate, methylparaben, propylparaben, sodium benzoate and the like. Presently preferred preservatives are benzalkonium chloride and thimerosal, particularly benzalkonium chloride.

The term "antioxidant" refers to a compound or mixture of compounds used in a formulation which is useful for preventing the oxidation of active compound(s) in a formulation. A antioxidant must be pharmaceutically acceptable at the concentrations used, and should not interfere with the action of the active compound in the formulation. An "effective amount" of an antioxidant is that amount necessary to prevent undue oxidation of the active compound under normal storage conditions. Presently preferred antioxidants are BHA, and BHT, particularly BHT.

The term "stabilizer" refers to a compound used in a formulation to prevent chemical degradation by means other than oxidation or microbial digestion. An "effective amount" of an oxidant is that amount necessary to prevent unacceptable degradation of the active compound. The presently preferred stabilizer is disodium EDTA.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

ADMINISTRATION

The compositions of the invention are advantageously administered intranasally by means of a "non-propellant" type aerosol or atomizer, especially using a pump-type dispenser. For example, the Calmar Mark II nasal pump (Calmar-Albert GmbH) and the Pfeiffer pump (Ing.-erich Pfeiffer GmbH & Co. KG) are generally useful.

Preferably, the aerosol pump will deliver a spray in which less than 1% of the droplets are below 16 μm in diameter. This minimizes the amount of composition which reaches the lungs.

PREPARATION

Compositions of the invention may be prepared as follows:

The desired amounts of propylene glycol, PEG 400, and polysorbate 20 are mixed well in an appropriate vessel. To this mixture is added the desired amount of flunisolide (preferably in the form of the hemihydrate), and BHT. The resulting mixture is heated to 50°–55° C. and mixed until the flunisolide and BHT dissolve.

The desired amount of sorbitol (e.g., as a 70% solution) is mixed with citric acid and sodium citrate (in the proper proportions for obtaining the desired buffer), benzalkonium chloride (e.g. as a 50% solution), edetate disodium, and water, to form a solution which is approximately 90% water. This solution is then mixed with the flunisolide solution and the pH measured and adjusted with HCl solution or NaOH solution as appropriate.

The resulting solution is brought to final volume with purified water, filtered through a 3 micron filter, and packaged.

EXAMPLE 1

(Example Formulations)

The following are representative compositions of the invention. The compositions are prepared as described in the Preparation above.

| Compound | amount % (w/v) |
|---|---|
| (A) | |
| flunisolide hemihydrate | 0.025 |
| propylene glycol | 5.0 |
| PEG 400 | 20.0 |
| polysorbate 20 | 2.50 |
| benzalkonium chloride | 0.035 |
| disodium EDTA | 0.01 |
| BHT | 0.01 |
| citric acid | 0.005 |
| sodium citrate.2H$_2$O | 0.00765 |
| sorbitol | 2.00 |
| water qs | 100.0 |
| pH | 5.2 |
| (B) | |
| flunisolide hemihydrate | 0.01 |
| propylene glycol | 2.0 |
| PEG 400 | 10.0 |
| polysorbate 20 | 1.0 |
| benzalkonium chloride | 0.03 |
| disodium EDTA | 0.01 |
| BHT | 0.01 |
| citric acid | 0.005 |
| sodium citrate.2H$_2$O | 0.00765 |
| sorbitol | 2.00 |
| water qs | 100.0 |
| pH | 5.3 |
| (C) | |
| beclomethasone | 0.05 |
| propylene glycol | 10.0 |
| PEG 400 | 25.0 |
| polysorbate 20 | 4.0 |
| benzalkonium chloride | 0.03 |
| disodium EDTA | 0.01 |
| BHT | 0.01 |
| citric acid | 0.005 |
| sodium citrate.2H$_2$O | 0.00765 |
| sorbitol | 5.00 |
| water qs | 100.0 |
| pH | 5.2 |

EXAMPLE 2

(Nasal Acceptability)

The following example illustrates a procedure for assaying the nasal acceptability of various compositions.

Eighteen volunteers were randomly divided into two groups. Group 1 received formulations A, B, and D. Group 2 received formulations A, C, and E. The tests were performed by applying one spray to each nostril, with a rest period of 4 hours between administrations of different formulations.

The following parameters were recorded, both immediately and 15 minutes after administration: nasal stinging, taste, other sensations, and willingness to use the spray three times daily. The formulations tested were as follows:

| | amount % (w/v) | | | | |
|---|---|---|---|---|---|
| Compound | A | B | C | D | E |
| propylene glycol | 20.0 | 7.0 | 5.0 | 0.0 | 0.0 |
| PEG 3350 | 15.0 | 0.0 | 0.0 | 0.0 | 0.0 |
| PEG 400 | 0.0 | 40.0 | 20.0 | 15.0 | 0.0 |
| polysorbate 20 | 0.0 | 0.0 | 2.50 | 3.5 | 3.5 |
| benzalkonium Cl | 0.02 | 0.02 | 0.02 | 0.02 | 0.02 |
| disodium EDTA | 0.01 | 0.01 | 0.01 | 0.01 | 0.01 |
| BHA | 0.002 | 0.002 | 0.002 | 0.002 | 0.002 |
| citric acid | 0.005 | 0.005 | 0.005 | 0.005 | 0.005 |
| Na citrate | 0.0077 | 0.0077 | 0.0077 | 0.0077 | 0.0077 |
| sorbitol | 0.0 | 3.0 | 2.0 | 2.0 | 2.0 |
| water qs | 100.0 | 100.0 | 100.0 | 100.0 | 100.0 |
| pH | 5.3 | 5.3 | 5.3 | 5.3 | 5.3 |

The results indicated superior nasal acceptability for compositions C, D, and E.

EXAMPLE 3

(Accelerated Stability)

The stability of formulations was investigated as follows:

Six formulations were prepared as set out below for testing. Ten mL of each formulation was filled and sealed in amber glass ampoules and stored at 80° C. (½ month), 60° C. (1.5 months), and 15° C. for the period of time stated. In addition, 25 mL of each solution was filled in 1 oz round high density polyethylene bottles and screw capped. These bottles were stored at 50° C. (2, 3, 8, and 10 months), 40° C. (8 and 10 months), and room temperature (RT) (8 and 10 months). At the end of the appropriate time period, the steroid content was determined using HPLC, and the pH of the solution measured. The results are normalized against the 15° C. data for the appropriate time periods.

| | amount % (w/v) Composition | | | | | | |
|---|---|---|---|---|---|---|---|
| | 1 | 2 | 3 | 4 | 5 | 6 | 7 |
| PG | 20.0 | 5.0 | 5.0 | 0.0 | 5.0 | 5.0 | 0.0 |
| PEG 3350 | 15.0 | 0.0 | 0.0 | 0.0 | 0.0 | 0.0 | 0.0 |
| PEG 400 | 0.0 | 20.0 | 20.0 | 15.0 | 20.0 | 20.0 | 15.0 |
| PS 20 | 0.0 | 2.5 | 2.5 | 3.5 | 2.5 | 2.5 | 3.5 |
| BHA | 0.01 | 0.01 | 0.01 | 0.01 | 0.0 | 0.0 | 0.0 |
| BHT | 0.0 | 0.0 | 0.0 | 0.0 | 0.01 | 0.01 | 0.01 |
| citrate | 0.01 | 0.01 | 0.02 | 0.01 | 0.02 | 0.01 | 0.02 |
| water qs | 100.0 | 100.0 | 100.0 | 100.0 | 100.0 | 100.0 | 100.0 |

In addition, each formulation contained 0.025% flunisolide, 2% sorbitol, 0.01% EDTA, and 0.04% benzalkonium chloride. Composition 1 corresponds to Composition A of Example 2. Compositions 2, 3, 5, and 6 are equivalent to Composition C of Example 2. Compositions 4 and 7 are equivalent to Composition D of Example 2.

The results indicated that the formulations of the invention (Compositions 2, 3, 5, and 6) display superior stability as compared to other compositions (1, 4, and 7) in this assay.

EXAMPLE 4

(Preservative Efficacy)

The compositions listed below are tested for preservative efficacy using the USP-BP modified double challenge test.

| | amount % (w/v) Composition | | | | |
|---|---|---|---|---|---|
| | A | B | C | D | E |
| flunisolide | 0.025 | 0.025 | 0.025 | 0.025 | 0.025 |
| propylene glycol | 20.0 | 7.0 | 5.0 | 0.0 | 0.0 |
| PEG 3350 | 15.0 | 0.0 | 0.0 | 0.0 | 0.0 |
| PEG 400 | 0.0 | 40.0 | 20.0 | 15.0 | 0.0 |
| polysorbate 20 | 0.0 | 0.0 | 2.50 | 3.5 | 3.5 |
| disodium EDTA | 0.01 | 0.01 | 0.01 | 0.01 | 0.01 |
| BHA | 0.002 | 0.002 | 0.002 | 0.002 | 0.002 |
| citrate buffer | 0.01 | 0.01 | 0.01 | 0.01 | 0.01 |
| sorbitol | 0.0 | 3.0 | 2.0 | 2.0 | 2.0 |
| water qs | 100.0 | 100.0 | 100.0 | 100.0 | 100.0 |
| pH | 5.3 | 5.3 | 5.3 | 5.3 | 5.3 |

In addition, each composition is prepared with 0.01, 0.02, 0.025, 0.03, 0.035, or 0.04% (w/v) benzalkonium chloride. These compositions correspond to compositions A-E of Example 2.

Compositions A-E are prepared, added to culture media, and the resulting test media directly inoculated with challenge organisms. After incubation for 14 days, the test media are inoculated again. The number of colony forming units is recorded over the remaining 14 days of the test.

The results indicated that Compositions A and B were effectively preserved with 0.01% benzalkonium chloride and Composition C was effectively preserved with 0.03% benzalkonium chloride, whereas Composition D required more than 0.04% benzalkonium chloride, and Composition E was not effectively preserved with any concentration of benzalkonium chloride tested.

What is claimed:

1. A stable, effectively preservable, substantially non-stinging aqueous anti-inflammatory steroid formulation suitable for intranasal administration, which formulation comprises:
   an anti-inflammatory steroid in an amount between about 0.01% and about 0.05% (w/v);
   propylene glycol in an amount between about 2% and about 10% (w/v);
   PEG 400 in an amount between about 10% and about 25% (w/v);
   polysorbate 20 in an amount between about 1% and about 4% (w/v);
   an effective amount of preservative;
   an effective amount of antioxidant;
   an effective amount of stabilizer;
   water; and
   pH buffering agent sufficient to adjust the pH of the resulting solution to between about 3.5 and about 7.

2. The formulation of claim 1 which comprises:

| | |
|---|---|
| Flunisolide (hemihydrate) | 0.0255% (w/v) |
| Propylene Glycol | 5.0% (w/v) |
| PEG 400 | 20.0% (w/v) |
| Polysorbate 20 | 2.50% (w/v) |
| Benzalkonium Chloride (50%) | 0.07% (w/v) |
| Edetate Disodium | 0.01% (w/v) |
| Butylated Hydroxyanisole | 0.01% (w/v) |
| Butylated Hydroxytoluene | 0.01% (w/v) |
| Citric Acid (Anhydrous) | 0.005% (w/v) |
| Trisodium Citrate Dihydrate | 0.00765% (w/v) |
| Sorbitol (70%) | 2.86% (w/v) |
| Purified Water, q.s. to | 100.0 and |
| adjust pH to | 5.3. |

3. The formulation of claim 1 which comprises:
   preservative in an amount between about 0.02% and about 0.08% (w/v);
   antioxidant in an amount between about 0.001% and about 0.05% (w/v); and
   stabilizer in an amount between about 0.005% and about 0.05% (w/v).

4. The formulation of claim 3 wherein said anti-inflammatory steroid is flunisolide in an amount of about 0.025% (w/v).

5. The formulation of claim 4 wherein:
   said preservative is benzalkonium chloride;
   said stabilizer is disodium EDTA; and
   said antioxidant is BHT.

6. The formulation of claim 5 which further comprises sorbitol in an amount between about 0.001% and about 5% (w/v).

7. The formulation of claim 6 wherein said pH buffering agent comprises:
   citric acid in an amount between about 0.001% and about 0.05% (w/v); and
   sodium citrate dihydrate in an amount between about 0.001% and about 0.05% (w/v).

8. A stable, effectively preservable, substantially non-stinging aqueous anti-inflammatory steroid formulation suitable for intranasal administration, which formulation comprises:
   flunisolide hemihydrate in an amount of about 0.025% (w/v);
   propylene glycol in an amount of about 5% (w/v);
   PEG 400 in an amount of about 20% (w/v);
   polysorbate 20 in an amount of about 2.50% (w/v);
   benzalkonium chloride in an amount of about 0.035% (w/v);
   disodium EDTA in an amount of about 0.01% (w/v);
   BHT in an amount of about 0.01% (w/v);
   citric acid in an amount of about 0.005% (w/v);
   sodium citrate dihydrate in an amount of about 0.00765% (w/v);
   sorbitol in an amount of about 2.00% (w/v); and
   water, wherein the pH of the resulting solution is adjusted to about 5.2.

9. A method of treating inflammation of the nasal mucosa without inducing stinging, which method comprises intranasally administering to a subject in need thereof a substantially non-stinging aqueous anti-inflammatory steroid formulation comprising
   an anti-inflammatory steroid in an amount between about 0.01% and about 0.05% (w/v);
   propylene glycol in an amount between about 2% and about 10% (w/v);
   PEG 400 in an amount between about 10% and about 25% (w/v);
   polysorbate 20 in an amount between about 1% and about 4% (w/v);
   an effective amount of preservative;
   an effective amount of antioxidant;
   an effective amount of stabilizer;
   water; and pH buffering agent sufficient to adjust the pH of the resulting solution to between about 3.5 and about 7.

10. The method of claim 9 wherein said formulation comprises:
preservative in an amount between about 0.02% and about 0.08% (w/v);
antioxidant in an amount between about 0.001% and about 0.05% (w/v); and
stabilizer in an amount between about 0.005% and about 0.05% (w/v).

11. The method of claim 10 wherein said anti-inflammatory steroid is flunisolide in an amount of about 0.025% (w/v).

12. The method of claim 11 wherein:
said preservative comprises benzalkonium chloride;
said stabilizer comprises disodium EDTA; and
said antioxidant comprises BHT.

13. The method of claim 12 which further comprises sorbitol in an amount between about 0.001% and about 5% (w/v).

14. The method of claim 13 wherein said pH buffering agent comprises:
citric acid in an amount between about 0.001% and about 0.05% (w/v); and
sodium citrate dihydrate in an amount between about 0.001% and about 0.05% (w/v).

15. A method of treating inflammation of the nasal mucosa without inducing stinging, which method comprises intranasally administering to a subject in need thereof a substantially non-stinging aqueous anti-inflammatory steroid formulation comprising
flunisolide hemihydrate in an amount of about 0.025% (w/v);
propylene glycol in an amount of about 5% (w/v);
PEG 400 in an amount of about 20% (w/v);
polysorbate 20 in an amount of about 2.50% (w/v);
benzalkonium chloride in an amount of about 0.035% (w/v);
disodium EDTA in an amount of about 0.01% (w/v);
BHT in an amount of about 0.01% (w/v);
citric acid in an amount of about 0.005% (w/v);
sodium citrate dihydrate in an amount of about 0.00765% (w/v);
sorbitol in an amount of about 2.00% (w/v); and
water, wherein the pH of the resulting solution is adjusted to about 5.2.

* * * * *